(12) United States Patent
Lentner et al.

(10) Patent No.: US 11,617,664 B1
(45) Date of Patent: Apr. 4, 2023

(54) ADJUSTABLE TRIAL FOR SIZING A SPINAL IMPLANT

(71) Applicant: Ortho Inventions, LLC, Palm Beach Gardens, FL (US)

(72) Inventors: Greg Lentner, Maumee, OH (US); John E. Hammill, Sr., Maumee, OH (US)

(73) Assignee: Ortho Inventions, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/936,034

(22) Filed: Sep. 28, 2022

Related U.S. Application Data

(60) Provisional application No. 63/277,833, filed on Nov. 10, 2021.

(51) Int. Cl.
    *A61F 2/46*     (2006.01)
    *A61F 2/44*     (2006.01)
    *A61F 2/30*     (2006.01)

(52) U.S. Cl.
CPC .......... *A61F 2/4684* (2013.01); *A61F 2/4465* (2013.01); *A61F 2002/3008* (2013.01); *A61F 2002/3023* (2013.01); *A61F 2002/3054* (2013.01); *A61F 2002/30153* (2013.01); *A61F 2002/30492* (2013.01); *A61F 2002/4668* (2013.01); *A61F 2310/00017* (2013.01); *A61F 2310/00023* (2013.01)

(58) Field of Classification Search
CPC .......... A61F 2/44; A61F 2/4455; A61F 2/446; A61F 2/4465; A61F 2/447; A61F 2/46; A61F 2/4603; A61F 2/4611; A61F 2/4684; A61F 2002/4668
See application file for complete search history.

(56) References Cited

U.S. PATENT DOCUMENTS

| | | | | |
|---|---|---|---|---|
| 7,927,374 | B2* | 4/2011 | Duggal | A61F 2/4425 623/17.14 |
| 8,172,904 | B2* | 5/2012 | Duggal | A61B 17/1604 623/17.15 |
| 8,545,564 | B2* | 10/2013 | Errico | A61F 2/4611 623/17.14 |
| 8,940,047 | B2* | 1/2015 | Errico | A61F 2/442 623/17.15 |
| 9,028,550 | B2* | 5/2015 | Shulock | A61F 2/442 623/17.11 |
| 9,700,429 | B2* | 7/2017 | Errico | A61F 2/4684 |
| 9,814,600 | B2* | 11/2017 | Shulock | A61F 2/441 |
| 10,610,374 | B2* | 4/2020 | Shulock | A61F 2/441 |

(Continued)

FOREIGN PATENT DOCUMENTS

| | | | | |
|---|---|---|---|---|
| WO | WO-2008036502 | A2 * | 3/2008 | ......... A61B 17/1604 |
| WO | WO-2009021144 | A2 * | 2/2009 | ........... A61B 17/025 |

(Continued)

*Primary Examiner* — Eric S Gibson
(74) *Attorney, Agent, or Firm* — McHale & Slavin, P.C.

(57) ABSTRACT

An adjustable trial for spinal implant sizing. The trial has a first and second plate that is adjustable between zero and degrees by use of continuously sloped edges that interface with a positioning band having reciprocal sloped edges. Protrusions are attached to each plate and the positioning band, the rotation of which is used to change the angle of the plates. A tool used to rotate the protrusions is marked with the angle of movement.

10 Claims, 9 Drawing Sheets

(56) References Cited

U.S. PATENT DOCUMENTS

| | | | |
|---|---|---|---|
| 11,285,014 B1 * | 3/2022 | Josse | A61F 2/4455 |
| 11,452,614 B2 * | 9/2022 | Rogers | A61F 2/447 |
| 2004/0153158 A1 * | 8/2004 | Errico | A61F 2/4611 |
| | | | 623/17.14 |
| 2004/0158325 A1 * | 8/2004 | Errico | A61B 17/025 |
| | | | 606/247 |
| 2007/0088441 A1 * | 4/2007 | Duggal | A61B 17/1757 |
| | | | 623/17.16 |
| 2009/0069894 A1 * | 3/2009 | Duggal | A61F 2/4425 |
| | | | 623/17.11 |
| 2009/0099568 A1 * | 4/2009 | Lowry | A61F 2/4455 |
| | | | 606/90 |
| 2009/0143861 A1 * | 6/2009 | Errico | A61B 17/025 |
| | | | 623/17.11 |
| 2011/0046744 A1 * | 2/2011 | Errico | A61F 2/4425 |
| | | | 623/17.16 |
| 2013/0190875 A1 * | 7/2013 | Shulock | A61F 2/441 |
| | | | 623/17.12 |
| 2014/0336769 A1 * | 11/2014 | Errico | A61F 2/4684 |
| | | | 623/17.16 |
| 2015/0216676 A1 * | 8/2015 | Shulock | A61F 2/4611 |
| | | | 623/17.16 |
| 2016/0151170 A1 * | 6/2016 | Errico | A61F 2/4611 |
| | | | 623/17.16 |
| 2018/0064557 A1 * | 3/2018 | Shulock | A61F 2/442 |
| 2020/0078190 A1 * | 3/2020 | Rogers | A61F 2/4455 |
| 2020/0093603 A1 * | 3/2020 | Manwill | A61F 2/447 |
| 2021/0045891 A1 * | 2/2021 | Rogers | A61F 2/30749 |
| 2022/0133492 A1 * | 5/2022 | Josse | B25B 23/0021 |
| | | | 623/17.16 |
| 2022/0133493 A1 * | 5/2022 | Josse | A61F 2/4455 |
| | | | 623/17.11 |
| 2022/0133498 A1 * | 5/2022 | Josse | A61F 2/30771 |
| | | | 623/17.11 |
| 2022/0133499 A1 * | 5/2022 | Josse | A61F 2/4611 |
| | | | 623/17.16 |

FOREIGN PATENT DOCUMENTS

| | | | | |
|---|---|---|---|---|
| WO | WO-2020068445 A1 * | 4/2020 | | A61F 2/4455 |
| WO | WO-2020069238 A1 * | 4/2020 | | A61F 2/30771 |
| WO | WO-2022096910 A1 * | 5/2022 | | A61F 2/4425 |
| WO | WO-2022096912 A1 * | 5/2022 | | A61F 2/4425 |

* cited by examiner

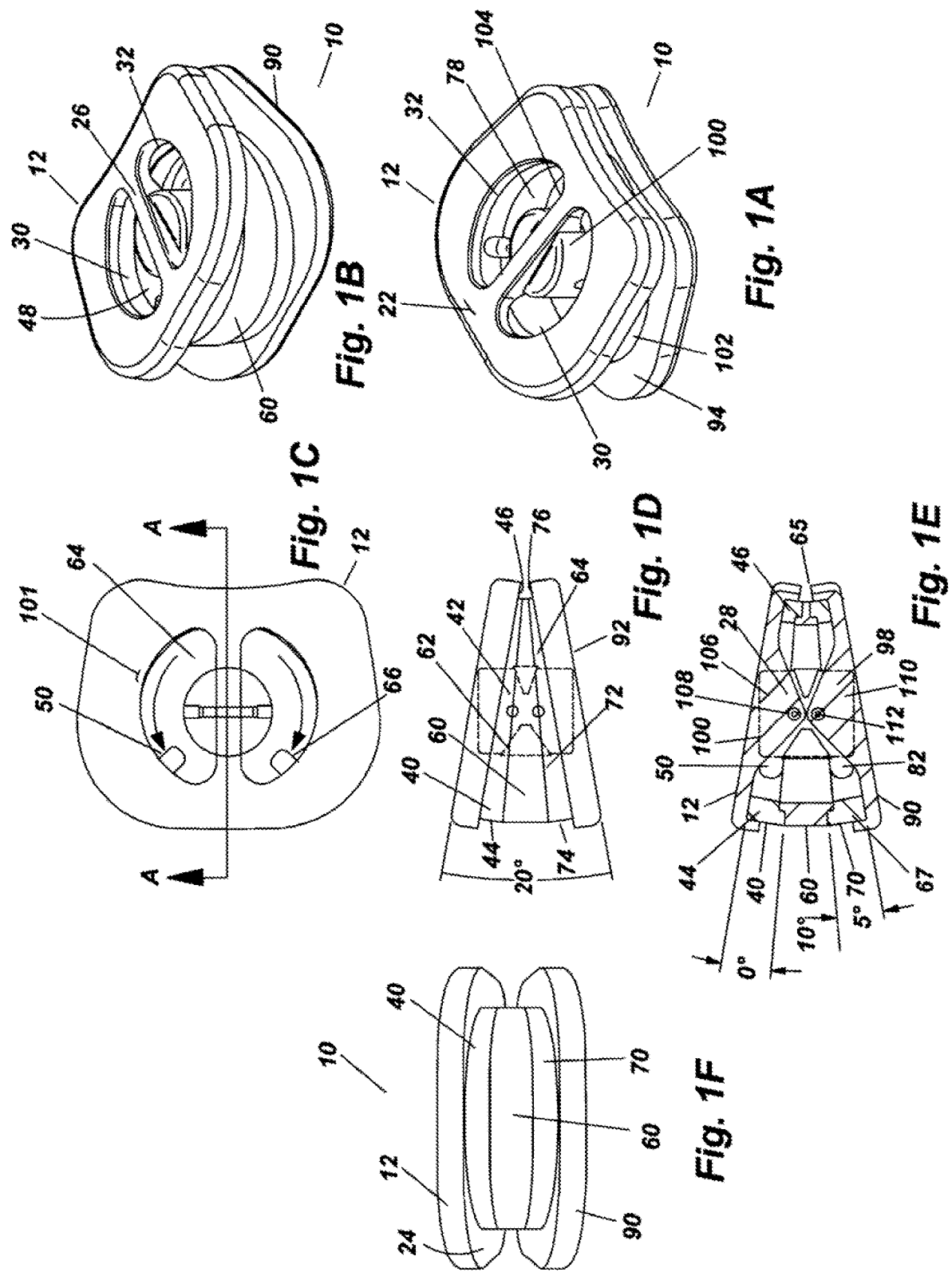

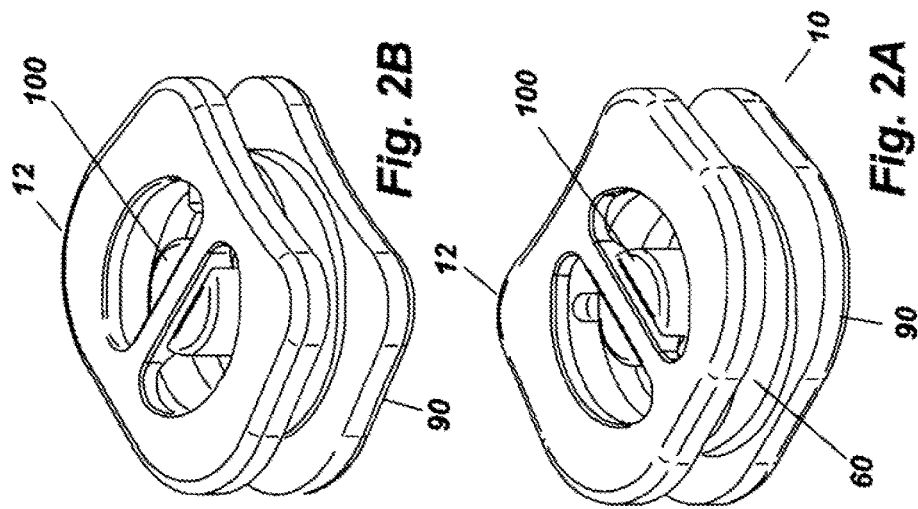
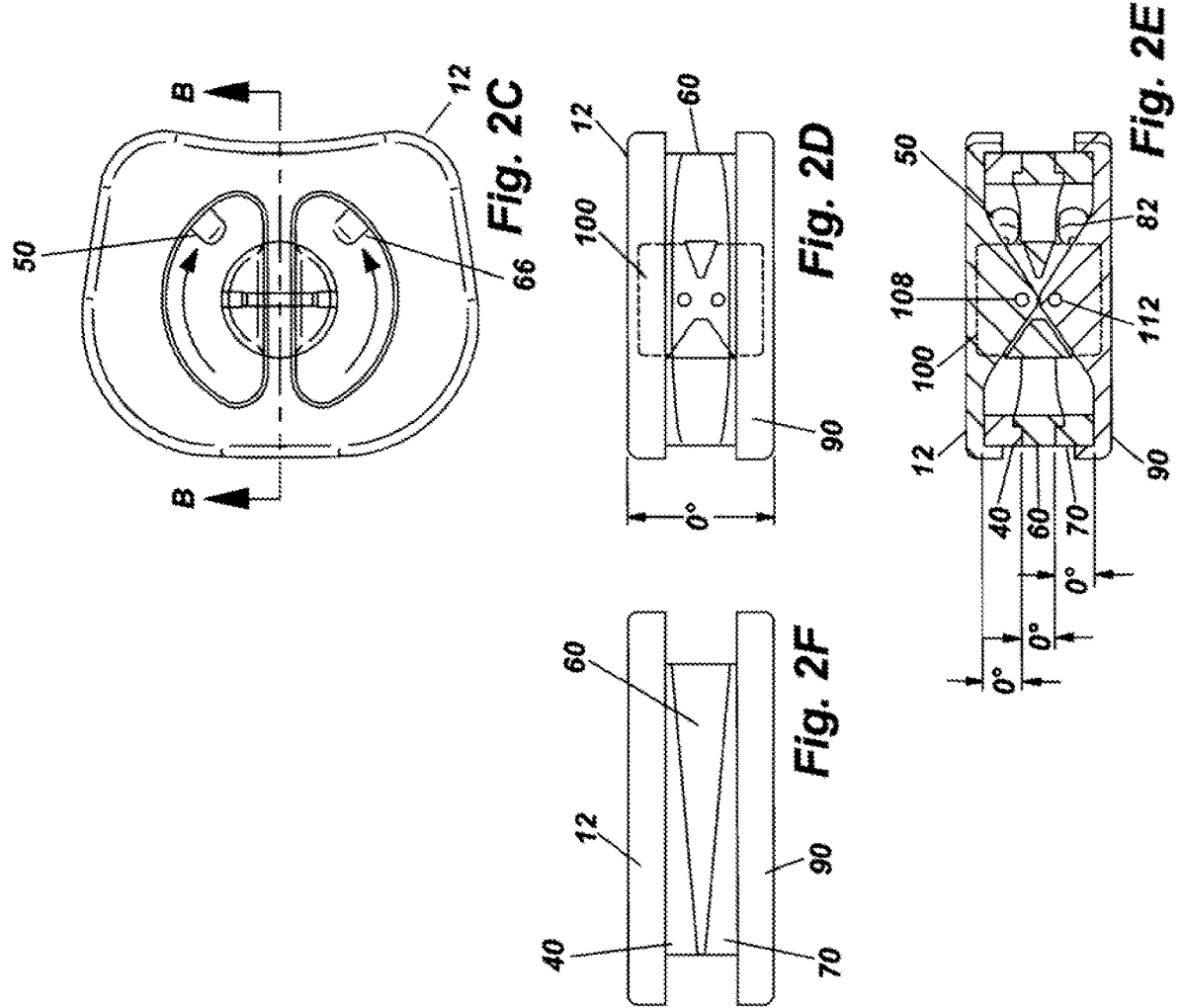

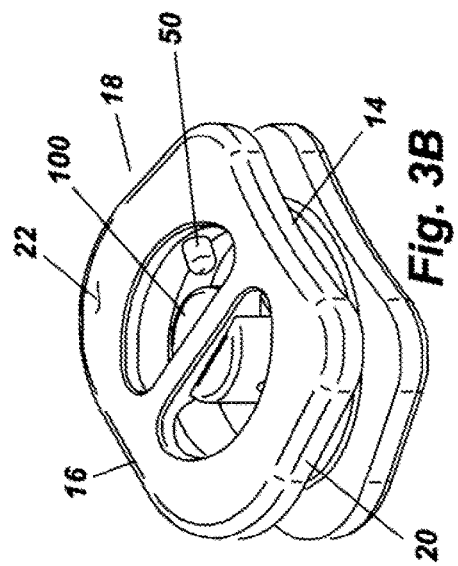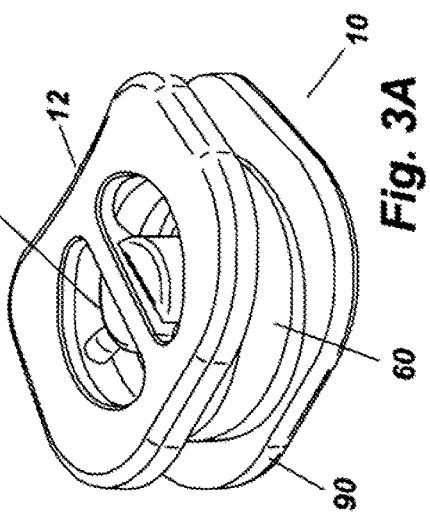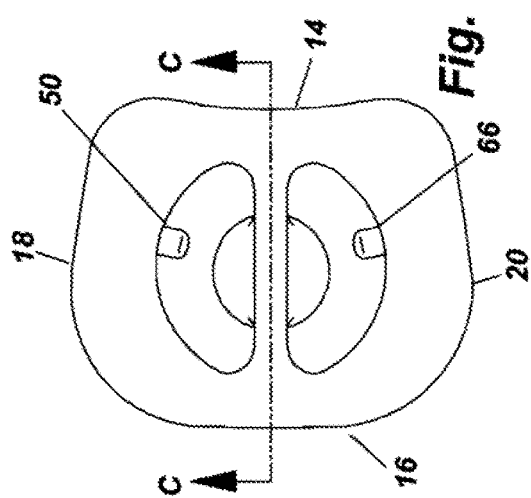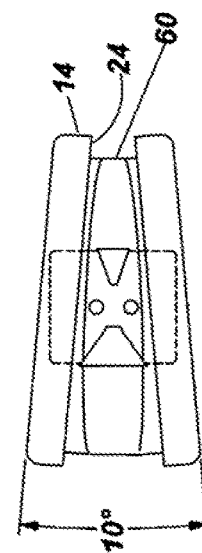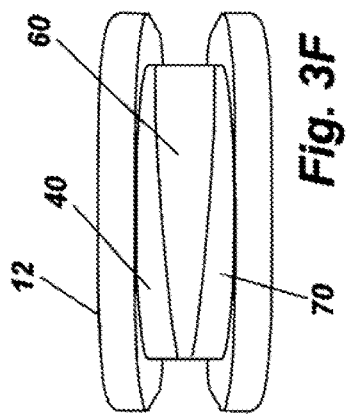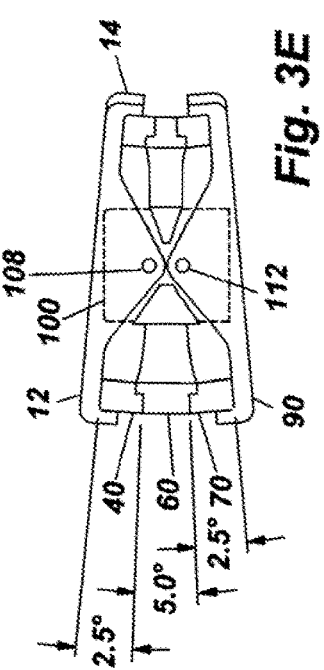

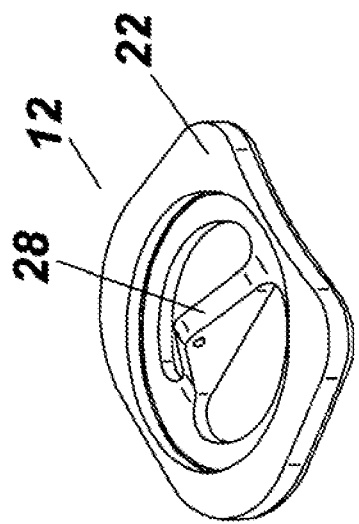
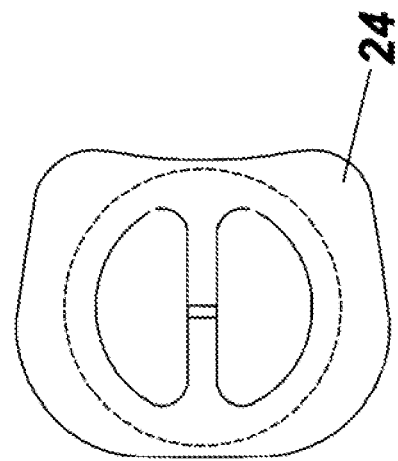
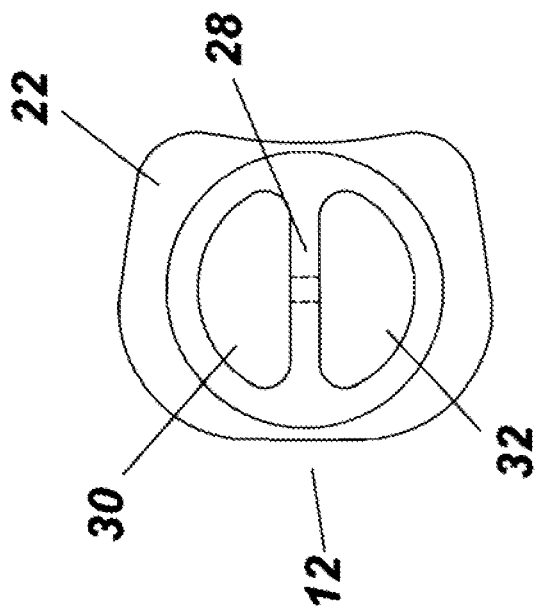
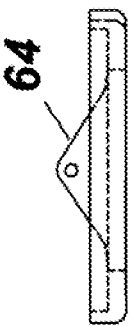
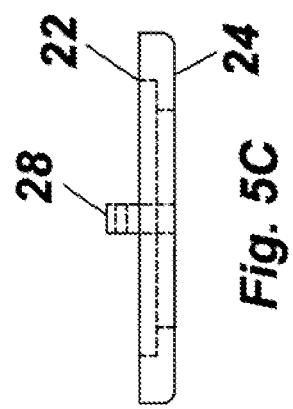

ADJUSTABLE TRIAL FOR SIZING A SPINAL IMPLANT

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 63/277,833, entitled "ADJUSTABLE TRIAL FOR SIZING A SPINAL IMPLANT", filed Nov. 10, 2021. The contents of which the above referenced application is incorporated herein by reference.

FIELD OF THE INVENTION

The present disclosure generally relates to medical devices for the treatment of musculoskeletal disorders, and more particularly to an adjustable trial to provide spinal implant sizing.

BACKGROUND OF THE INVENTION

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and/or aging. The front or anterior portions of adjacent vertebrae between which an intervertebral disc normally resides are referred to as "vertebral bodies." The anterior space between adjacent vertebral bodies where a disc normally resides is referred to as "intervertebral disc space." The vertebral bodies provide support and structure of the spine while spinal discs, located between the vertebrae, act as cushions. These discs contribute to the flexibility and motion of the spinal column. Over time, the spinal disorders may cause the discs to become diseased, infected, develop deformities such as tears/cracks, or simply lose structural integrity. These impaired discs can affect the anatomical functions of the vertebrae, due to the resultant lack of proper biomechanical support, and are often associated with chronic back pain, nerve damage and in severe cases partial or complete loss of mobility. In cases where an intervertebral disc becomes abnormal, the intervertebral disc is usually surgically removed and replaced with an intervertebral implant device into the vacated intervertebral disc space.

The common approach to the removal of a diseased intervertebral disc and replacement with an intervertebral implant is usually via a posterior or an anterior approach. Disc replacement surgery usually includes posterior laminectomy to first decompress the posterior neural elements and to gain access either through a direct posterior approach, or through a transpedicular approach, or through a posterior-lateral or transforaminal approach. After posterior exposure, the intervertebral disc is removed and the intervertebral disc space prepared to receive an implantable device inserted through a posterior-lateral approach or through a lateral transforaminal approach.

Commonly the intervertebral disc space is prepared to receive an implant by use of trials devices. Once the intervertebral disc is removed from the body during the lateral lumbar interbody fusion, the surgeon tries different sized trial implants to determine the appropriate size of the implant for maintaining a distance between the adjacent vertebrae. A trail implant kit conventionally holds numerous trail implants of various heights and geometric options to fit the anatomical needs of a patient. Another consideration is to maintain the natural angle between lumbar vertebral bodies to accommodate the lordosis, or natural curvature, of the spine. Therefore, during selection of an implant, both intervertebral disc height and lordosis must be considered.

A conventional trial implant kit contains multiple trial implants. Each implant preferably has a different shape and/or size, which is identical to, or similar to, a shape and size of an available prosthesis to be implanted. Each trial implant includes a body having a size and shape adapted to fit within or adjacent to an anatomical structure, and at least one marker strip associated with the body and formed from a radio-opaque material. This procedure is generally conducted using fluoroscopy and tactile feel.

What is lacking in the art is an adjustable trial for implant sizing.

SUMMARY OF THE INVENTION

An adjustable trial for spinal implant sizing formed a first plate having a substantially flat outer surface spaced apart from an inner surface with a centrally disposed coupling member extending outwardly from the inner surface. First and second apertures extend from the outer surface to the inner surface on each side of the coupling member. A first cylindrical shaped member is secured to the first plate having a continuous sloped edge with a converging angle. A centrally disposed aperture coincides with the first and second apertures of the first plate wherein a first protrusion extends into the first cylindrical shaped member aperture. A positioning band having a sloped upper surface and a sloped lower surface is rotatable with the continuous sloped edge of the first cylindrical shaped member forming a converging angle. The positioning band having a centrally disposed aperture that coincides with the first and second apertures of the first plate and employs a second protrusion extending into positioning band centrally disposed aperture. A second cylindrical shaped member rotatable having a continuous slope edge converging at an angle forming a mirror image to said first cylindrical shaped member, the second cylindrical shaped member having an aperture with an inner diameter that coincides with the positioning band aperture wherein a third protrusion extends into the aperture for alignment with the first protrusion. A second plate forming a mirror image of said first plate includes a substantially flat outer surface spaced apart from an inner surface which is secured to the second cylindrical shaped member. A coupling member extends outwardly from the inner surface and the second plate includes a first aperture and a second aperture placed in alignment with the first aperture and second aperture of the first plate. A coupling element having a top end is attached to the first plate by a pin; a bottom end of the coupling element is attached to the second plate by a second pin.

An objective of the invention is to provide an adjustable trial device determining the correct sized implant.

Another objective of the invention is to provide plates that are adjustable between an angle of zero degrees and 20 degrees.

Still another objective of the invention is to provide a tool that rotate protrusions to provide an angular reading.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1A is front perspective view of a fully expanded adjustable trial;
FIG. 1B is rear perspective view thereof;
FIG. 1C is top view thereof;
FIG. 1D is a side view thereof;
FIG. 1E is a cross sectional side view taken along section AA of FIG. 1C;
FIG. 1F is an end view thereof;
FIG. 2A is front perspective view of an unexpanded adjustable trial;
FIG. 2B is rear perspective view thereof;
FIG. 2C is top view thereof;
FIG. 2D is a side view thereof;
FIG. 2E is a cross sectional side view taken along section BB of FIG. 2C;
FIG. 2F is an end view thereof;
FIG. 3A is front perspective view of an unexpanded adjustable trial;
FIG. 3B is rear perspective view thereof;
FIG. 3C is top view thereof;
FIG. 3D is a side view thereof;
FIG. 3E is a cross sectional side view taken along section CC of FIG. 3C;
FIG. 3F is an end view thereof;
FIG. 5A is a top view of the first plate;
FIG. 5B is a bottom perspective view thereof;
FIG. 5C is a side view thereof;
FIG. 5D is an end view thereof;
FIG. 5E is a bottom view thereof.

DETAILED DESCRIPTION OF THE PREFERRED EMBODIMENT

Figure 4:
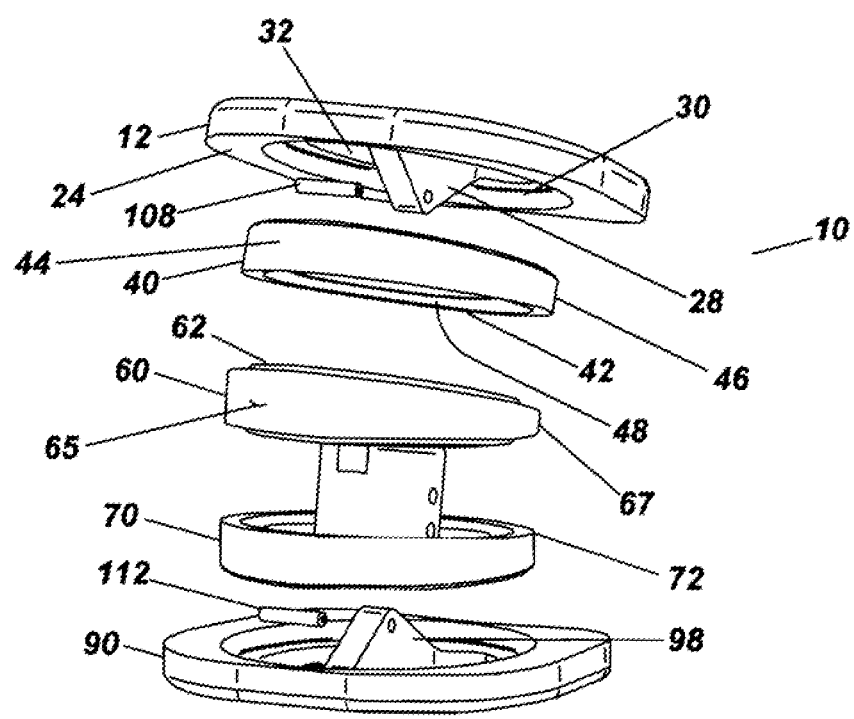
FIG. 4 is an exploded view of the adjustable trial.
Figure 6D:
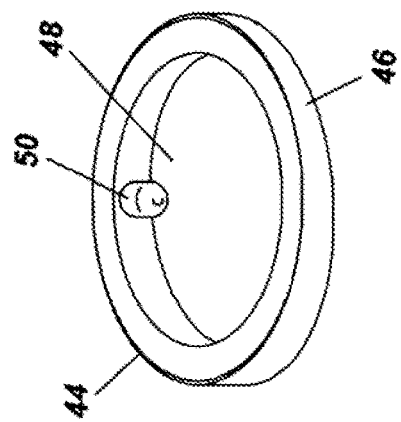
FIG. 6D is a perspective view thereof.
Figure 6A:
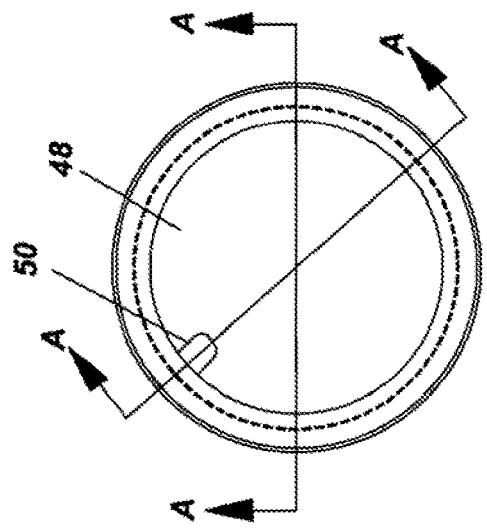
FIG. 6A is a top view of the positioning band.
Figure 6C:
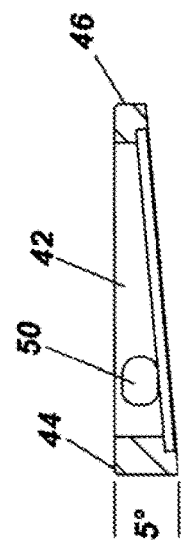
FIG. 6C is a cross sectional view taken allow lines B-B of FIG. 6A.
Figure 6B:
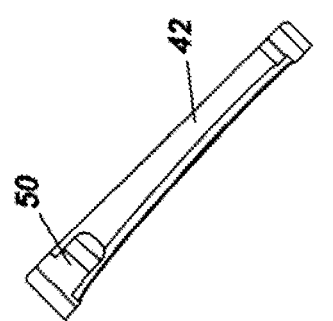
FIG. 6B is a cross sectional view taken allow lines A-A of FIG. 6A.
Figure 7D:
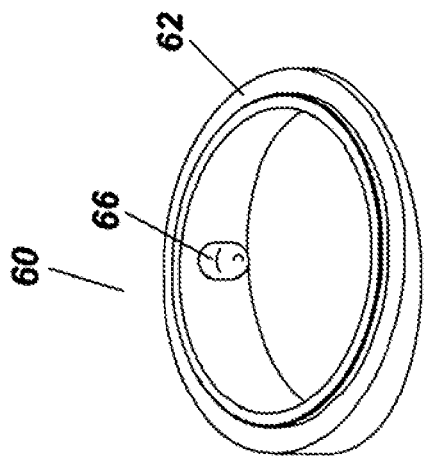
FIG. 7D is a perspective view thereof.
Figure 7A:
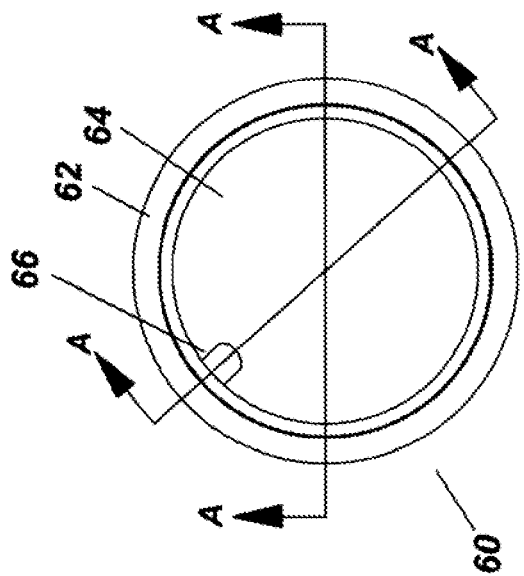
FIG. 7A is a top view of the first cylindrical member.
Figure 7B:
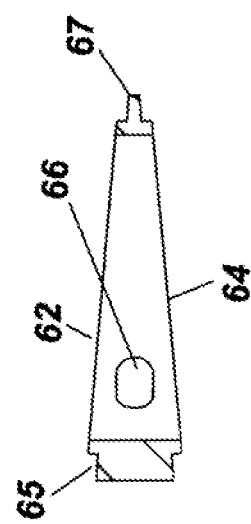
FIG. 7B is a cross sectional view taken allow lines A-A of FIG. 7A.
Figure 7C:
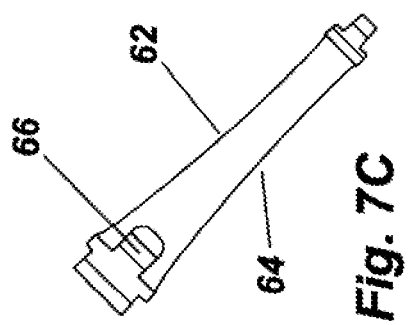
FIG. 7C is a cross sectional view taken allow lines B-B of FIG. 7A.
Figure 8D:
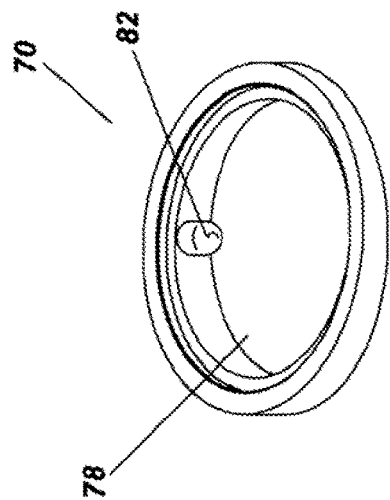
FIG. 8D is a perspective view thereof.
Figure 8A:
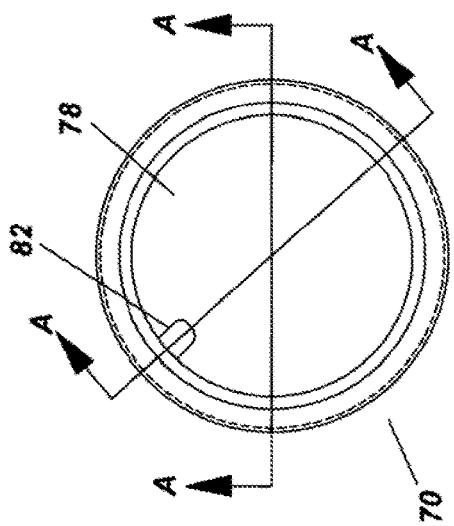
FIG. 8A is a top view of the second cylindrical member.
Figure 8B:
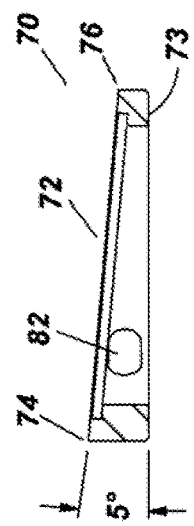
FIG. 8B is a cross sectional view taken allow lines A-A of FIG. 8A.
Figure 8C:
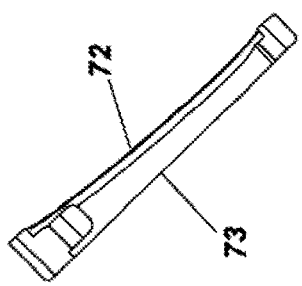
FIG. 8C is a cross sectional view taken allow lines B-B of FIG. 8A.
Figure 9A:
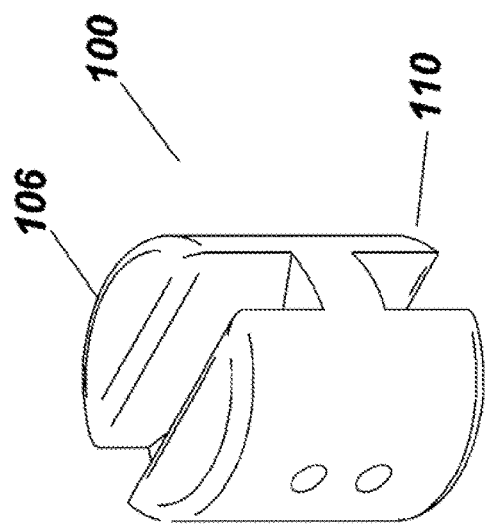
FIG. 9A is a perspective view of a coupling element.
Figure 9B:
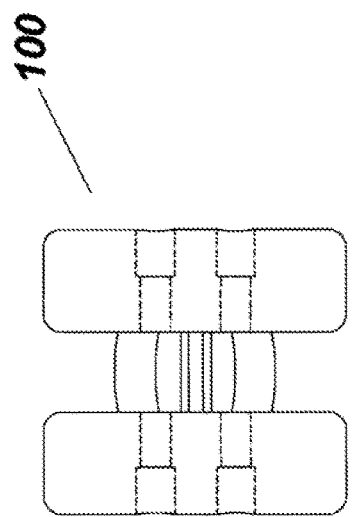
FIG. 9B is a top view thereof.
Figure 9C:
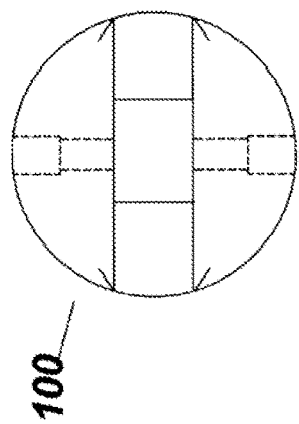
FIG. 9C is a front side view thereof.
Figure 9D:
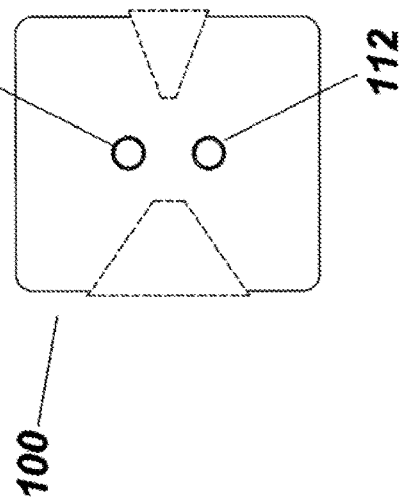
FIG. 9D is a right side view thereof.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

Now referring to the Figures, an adjustable trial 10 for spinal implant sizing is constructed from a first plate 12, FIGS. 5A-5E, having a substantially rectangular shape defined by a front edge 14, a rear edge 16 and opposing side edges 18 and 20. The first plate 12 further defined by a substantially flat outer surface 22 spaced apart from an inner surface 24 with a centrally disposed coupling member 28 extending outwardly from the inner surface 24. The first plate 12 having a first aperture 30 and a second aperture 32 extending from the outer surface 22 to the inner surface 24 formed on each side of the coupling member 28.

A first cylindrical shaped member 40, further depicted in FIGS. 6A-6D, is juxtapositioned along the inner surface 24 of the first plate 12. The first cylindrical member 40 having a continuous sloped edge 42 converging at an angle of about 5 degrees wherein a proximal end 44 has a thickness that is greater than a distal end 46 thickness. The first cylindrical shaped member 40 having a centrally disposed aperture 48 formed by an inner diameter that coincides with the first and second apertures 30, 32 of the first plate 12. A first protrusion 50 extends into the first cylindrical shaped member aperture 48 for use rotating the first cylindrical shaped member 40 changing the angular slope of the outer surface 22 of the first plate 12 so as to conform to the position of a spinal disc, not shown.

A positioning band 60, further illustrated in FIGS. 7A-7D, has a sloped upper surface 62 and a sloped lower surface 64. The sloped upper surface 62 is rotatable with the continuous sloped edge 42 of the first plate 12 formed between a proximal end 65 and a distal end 67 converging at an angle of about 10 degrees. The positioning band 60 having a centrally disposed aperture 64 that coincides with the first and second apertures 30, 32 of the first plate 12 and a second protrusion 66 extending into positioning band centrally disposed aperture 64 aligned with said second aperture 32 of said first plate 12. As will be further illustrated, rotation of the protrusions 50, 66 provides angular positioning of the first plate 12 and second plate 90.

A second cylindrical shaped member 70, further illustrated in FIGS. 8A-8D, having a continuous sloped edge 72 converging at an angle of about 5 degrees wherein a proximal end 74 has a thickness that is greater than a distal end 76 thickness with a lower edge 73. The continuous sloped edge 72 forming a mirror image to said first cylindrical shaped member sloped edge 42. The second cylindrical shaped member 70 having an aperture with an inner diameter that coincides with the positioning band aperture 64. A third protrusion 82 extending into the aperture 78 of said second cylindrical shaped member for adjustable alignment with the first protrusion 50 and second protrusion 66. Illustrated in FIGS. 1C, 2C and 3C, rotation of protrusions 50, 82 together in one direction and protrusion 66 in the other direction changes the lordosis angle.

A second plate 90 forming a mirror image of said first plate 12 having a substantially rectangular shape defined by a front edge, a rear edge and opposing side edges. The second plate 90 further includes a substantially flat outer surface 92 spaced apart from an inner surface 94 which is secured to the second cylindrical shaped member 70. A coupling member 98 extends outwardly from said inner surface 94. The second plate 90 having a first aperture 102 and a second aperture 104 placed in alignment with said first aperture 30 and said second aperture 32 of the first plate 12.

A coupling element 100, further illustrated in FIGS. 9A-9D, having a top end 106 attached to the first plate 12 by a pin 108, a bottom end 110 of the coupling element 100 is attached to the second plate 90 by a pin 112. A tool can be employed to maintain the first protrusion 50 and the third protrusion 82 in alignment while moving the second protrusion allowing said outer surface 22 of said first plate 12 and said outer surface 92 of said second plate 90 to vary from an angle of zero degrees to an angle of 20 degrees. Upon rotation of the first 50 and third protrusions 82, in relation to the second protrusion 66 results in the angular placement of the first and second plates which can be measured directly to allow sizing of the implant, or read from the tool used to move the protrusions wherein the position of the protrusions can be translated to markings on the tool allowing the tool to state the plate angle.

The trial implant 10 is formed from a material that is visible under radiographic imaging, such as titanium, stainless steel, or the like. Alternatively the implant is formed from materials such as polymers, ceramics, composite materials, and combinations thereof. Examples of suitable polymers include polyether sulfone, polycarbonate, and bioabsorbable polymers, and examples of suitable composites include carbon fiber reinforced polymers. The marker strip can also be formed from a variety of radio-opaque materials including, for example, metals, polymers, filling salts, ceramics, and combinations thereof. Examples of suitable metals include titanium, stainless steel, tantalum, cobalt chromium, aluminum, and combinations thereof. Marker strips may also be configured to indicate, on an x-ray image, the size and alignment of the body with respect to the anatomical structure when the implantable trial prosthesis is positioned within or adjacent to an anatomical structure. In use, the surgeon can select an implant from among several implants provided in the kit, and position and x-ray the implant to determine the fit. In the event that the selected trial implant does not fit appropriately, the surgeon simply rotate the protrusions to change the angle. Once the angle is selected the surgeon can then implant the appropriately sized implant for that particular patient.

Referring to FIGS. 1A-1F, illustrated is the adjustable trial 10 in an expanded position. FIGS. 1C and 1E depict the rotation of protrusions 50,82 in relation to protrusion place 66.

Referring to FIGS. 2A-2F, illustrated is the adjustable trial 10 in a contracted position. FIGS. 2C and 2E depict the rotation of protrusions 50,82 in relation to protrusion place 66.

Referring to FIGS. 3A-3F, illustrated is the adjustable trial 10 in a semi-expanded position. FIG. 4C depicts the rotation of protrusions 50,82 in relation to protrusion place 66. Indicia 101 may be placed on the adjustable trial to indicate lordosis angle in relation to the protrusion placement.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") are open-ended linking verbs. As a result, a device that "comprises," "has," "includes" or "contains" one or more steps or elements, possesses those one or more steps or elements, but is not limited to possessing only those one or more elements.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An adjustable trial for spinal implant sizing comprising:
a first plate having a substantially rectangular shape defined by a front edge, a rear edge and opposing side edges, the first plate having a substantially flat outer surface spaced apart from an inner surface with a centrally disposed coupling member extending outwardly from said inner surface, said first plate having a first aperture and a second aperture extending from said outer surface to said inner surface formed on each side of said coupling member;
a first cylindrical shaped member secured to said inner surface of said first plate having a continuous sloped edge converging angle, with a centrally disposed aperture formed by an inner diameter that coincides with said first and second apertures of said first plate, a first protrusion extends into said first cylindrical shaped member aperture aligned with said first aperture of said first plate;
a positioning band having a sloped upper surface and a sloped lower surface, said sloped upper surface being rotatable with said continuous sloped edge forming a converging angle, said positioning band having a centrally disposed aperture that coincides with said first and second apertures of said first plate and a second protrusion extending into the positioning band centrally disposed aperture and aligned with said second aperture of said first plate;
a second cylindrical shaped member having a continuous sloped edge converging angle, said continuous sloped edge forming a mirror image to said first cylindrical shaped member sloped edge, said second cylindrical shaped member having an aperture with an inner diameter that coincides with said positioning band aperture, a third protrusion extending into said aperture of said second cylindrical shaped member for alignment with said first protrusion;

a second plate forming a mirror image of said first plate having a substantially rectangular shape defined by a front edge, a rear edge and opposing side edges, said second plate further including a substantially flat outer surface spaced apart from an inner surface which is secured to said second cylindrical shaped member, a coupling member extending outwardly from said inner surface, said second plate having a first aperture and a second aperture placed in alignment with said first aperture and said second aperture of said first plate; and a coupling element having a top end attached to said first plate by a pin, a bottom end of said coupling element is attached to said second plate by a second pin;

wherein movement of said first, second and third protrusions changes a lordosis angle of said second plate.

2. The adjustable trial for spinal implant sizing according to claim 1 wherein a first cylindrical shaped ramp is formed integral with said first plate, and a second cylindrical shaped ramp is formed integral with said second plate.

3. The adjustable trial for spinal implant sizing according to claim 1 wherein said trial is constructed from a material that is visible under radiographic imaging.

4. The adjustable trial for spinal implant sizing according to claim 3 wherein said material is titanium or stainless steel.

5. The adjustable trial for spinal implant sizing according to claim 3 wherein said material is selected from the group consisting of polymers, ceramics, composite materials, and combinations thereof having a marker strip formed.

6. The adjustable trial for spinal implant sizing according to claim 1 wherein said converging angles of said first and second cylindrical shaped members are 5 degrees.

7. The adjustable trial for spinal implant sizing according to claim 1 wherein said converging angle of said positioning band is 10 degrees.

8. The adjustable trial for spinal implant sizing according to claim 1 wherein said first plate and said second plate can be rotated between zero degrees and 20 degrees.

9. The adjustable trial for spinal implant sizing according to claim 1 wherein said first plate and said first cylindrical shaped member forms a mirror image of and are interchangeable with said second plate and said second cylindrical shaped member.

10. The adjustable trial for spinal implant sizing according to claim 1 wherein indicia are provided to indicate the lordosis angle.

* * * * *